United States Patent [19]

Orrico

[11] Patent Number: 5,558,136
[45] Date of Patent: Sep. 24, 1996

[54] BONE CEMENT CARTRIDGE WITH SECONDARY PISTON

[75] Inventor: Michael R. Orrico, Kalamazoo, Mich.

[73] Assignee: Stryker Corporation, Kalamazoo, Mich.

[21] Appl. No.: 189,328

[22] Filed: Jan. 31, 1994

[51] Int. Cl.⁶ ................................................ A61B 17/56
[52] U.S. Cl. ............................ 141/23; 141/27; 222/327; 606/93
[58] Field of Search .................................. 222/326, 327, 222/386, 389; 141/21–27; 366/139; 606/92–94

[56] References Cited

U.S. PATENT DOCUMENTS

| | | |
|---|---|---|
| D. 261,425 | 10/1981 | Bruhn . |
| 368,704 | 8/1887 | Bryant . |
| 546,073 | 8/1895 | Mix . |
| 2,095,543 | 10/1937 | Doll . |
| 2,157,217 | 5/1939 | Rauch . |
| 2,224,967 | 12/1940 | Kaye . |
| 2,570,079 | 10/1951 | Spremulli . |
| 2,732,102 | 1/1956 | Ekins . |
| 2,750,943 | 6/1956 | Dann . |
| 2,778,541 | 1/1957 | Sherbondy . |
| 2,838,210 | 6/1958 | Detrie et al. . |
| 3,058,632 | 10/1962 | Stremmel . |
| 3,095,914 | 7/1963 | Bachmann ................................ 141/27 |
| 3,112,743 | 12/1963 | Cochran et al. . |
| 3,141,583 | 7/1964 | Mapel et al. . |
| 3,160,156 | 12/1964 | Tyler . |
| 3,193,146 | 7/1965 | Isgriggs et al. . |
| 3,255,747 | 6/1966 | Cochran et al. . |
| 3,290,017 | 12/1966 | Davies et al. . |
| 3,330,282 | 7/1967 | Visser et al. ............................ 141/27 X |
| 3,368,592 | 2/1968 | Thiel et al. . |
| 3,422,814 | 1/1969 | Lloyd . |
| 3,721,229 | 3/1973 | Panzer . |
| 3,739,947 | 6/1973 | Baumann et al. . |
| 3,742,724 | 7/1973 | Carpigiani . |
| 3,765,413 | 10/1973 | Lepar . |
| 3,815,878 | 6/1974 | Baskas et al. . |
| 3,894,663 | 7/1975 | Carhart et al. . |
| 3,907,106 | 9/1975 | Purrmann et al. . |
| 3,967,759 | 7/1976 | Baldwin et al. ..................... 222/386 X |
| 4,090,639 | 5/1978 | Campbell et al. . |
| 4,138,816 | 2/1979 | Warden et al. . |
| 4,208,133 | 6/1980 | Korte-Jungermann . |
| 4,277,184 | 7/1981 | Solomon . |
| 4,338,925 | 7/1982 | Miller . |
| 4,405,249 | 9/1983 | Scales . |
| 4,515,267 | 5/1985 | Welsh . |
| 4,546,767 | 10/1985 | Smith . |
| 4,576,152 | 3/1986 | Muller et al. . |
| 4,671,263 | 6/1987 | Draenert . |
| 4,676,655 | 6/1987 | Handler . |

(List continued on next page.)

FOREIGN PATENT DOCUMENTS

| | | |
|---|---|---|
| 1163504 | 2/1964 | Germany . |
| 372885 | 12/1963 | Switzerland . |

OTHER PUBLICATIONS

Stryker Case 99, Serial No. 07/769 004–Drawings (8 sheets) Figs. 1–6.

Stryker Case 100, Serial No. 07/769 003–Drawings (5 sheets) Figs. 1–10.

*Primary Examiner*—J. Casimer Jacyna
*Attorney, Agent, or Firm*—Flynn, Thiel, Boutell & Tanis, P.C.

[57] ABSTRACT

A surgical cement cartridge, for loading with surgical cement and for ejecting surgical cement at a surgical site, comprises a substantially tubular casing comprising a peripheral wall surrounding a longitudinal passage, the passage having an open front end and a remote rear end. A first piston unit is located in the passage for free sliding movement from the front end towards the rear end in response to input of surgical cement into the front end of the casing. A second piston unit is located in the passage adjacent the rear end for forcible driving forward along the passage to cause the first piston unit to eject cement from the first casing end toward a surgical site, the second piston unit having seal mechanism for positively blocking flow of surgical cement axially therepast.

16 Claims, 7 Drawing Sheets

U.S. PATENT DOCUMENTS

| | | |
|---|---|---|
| 4,721,390 | 1/1988 | Lidgren . |
| 4,723,581 | 2/1988 | Staudenrausch et al. . |
| 4,758,096 | 7/1988 | Gunnarsson . |
| 4,787,751 | 11/1988 | Bakels . |
| 4,815,454 | 3/1989 | Dozier, Jr. . |
| 4,966,601 | 10/1990 | Draenert ................................. 606/92 |
| 4,973,168 | 11/1990 | Chan . |
| 4,994,065 | 2/1991 | Gibbs et al. . |
| 5,015,101 | 5/1991 | Draenert . |
| 5,052,243 | 10/1991 | Tepic . |
| 5,265,956 | 11/1993 | Nelson et al. ......................... 366/139 |

BONE CEMENT CARTRIDGE WITH SECONDARY PISTON

FIELD OF THE INVENTION

This invention relates to surgical cement mixing and injecting apparatus, and more particularly an improved cartridge for surgical cement, for example two part bone cement suitable for fixing a prosthesis to bone in a surgical patient.

BACKGROUND OF THE INVENTION

In orthopedic procedures it is common to use a surgical cement, such as an acrylic bone cement, to affix a prosthesis to the bone, for example to fix a hip joint implant to the interior surfaces of the femoral canal.

U.S. application Ser. No. 07/769 004 filed Sep. 30, 1991 and a co-pending divisional thereof, namely U.S. Ser. No. 08/132 031 filed Oct. 5, 1993, both assigned to the assignee of the present invention, disclose an advantageous apparatus for mixing such cement and loading it by gravity into a cartridge. The mixing and loading are carried out under subatmospheric pressure to minimize air or other gas bubbles in the mixed cement. The cartridge, loaded with cement, is then transferred to a bone cement injection device (conveniently referred to as a gun). One such bone cement injection device has a pistol-shaped body for releasably supporting a forward extending cartridge containing bone cement and further having a ram actuable by a manually moveable trigger for pushing bone cement out the front of the cartridge through a suitable nozzle and into the femoral cavity. For example, such a gun is disclosed in U.S. application Ser. No. 07/769 003 assigned to the assignee of the present invention.

The mixing and loading apparatus shown in the aforementioned U.S. application Ser. No. 07/769 004 and the injection device shown in above referenced U.S. application Ser. No. 07/769 003 have been successfully marketed for more than a year prior to the filing date of the present application.

The present invention arises from a continuing effort on the part of the present assignee to improve surgical cement, particularly bone cement, mixing and injecting apparatus and particularly to improve cartridges useable with such apparatus.

Further objects and purposes of the present invention will be apparent to persons acquainted with apparatus of this general type upon reading the following specification and inspecting the accompanying drawings.

SUMMARY OF THE INVENTION

A surgical cement cartridge, for loading with surgical cement and for ejecting surgical cement at a surgical site, comprises a substantially tubular casing comprising a peripheral wall surrounding a longitudinal passage, the passage having an open front end and a remote rear end. A first piston unit is located in the passage for free sliding movement from the front end towards the rear end in response to input of surgical cement into the front end of the casing. A second piston unit is located in the passage adjacent the rear end for forcible driving forward along the passage to cause the first piston unit to eject cement from the first casing end toward a surgical site, the second piston unit having seal mechanism for positively blocking flow of surgical cement axially therepast.

DETAILED DESCRIPTION

A bone cement mixing and loading apparatus 10 (FIGS. 1 and 2) comprises a mixing chamber 11 and a cartridge 12 located below the mixing chamber for receiving mixed bone cement therefrom. A vacuum shroud 13 (FIGS. 1 and 5) supports the mixing chamber and cartridge.

Figure 1:
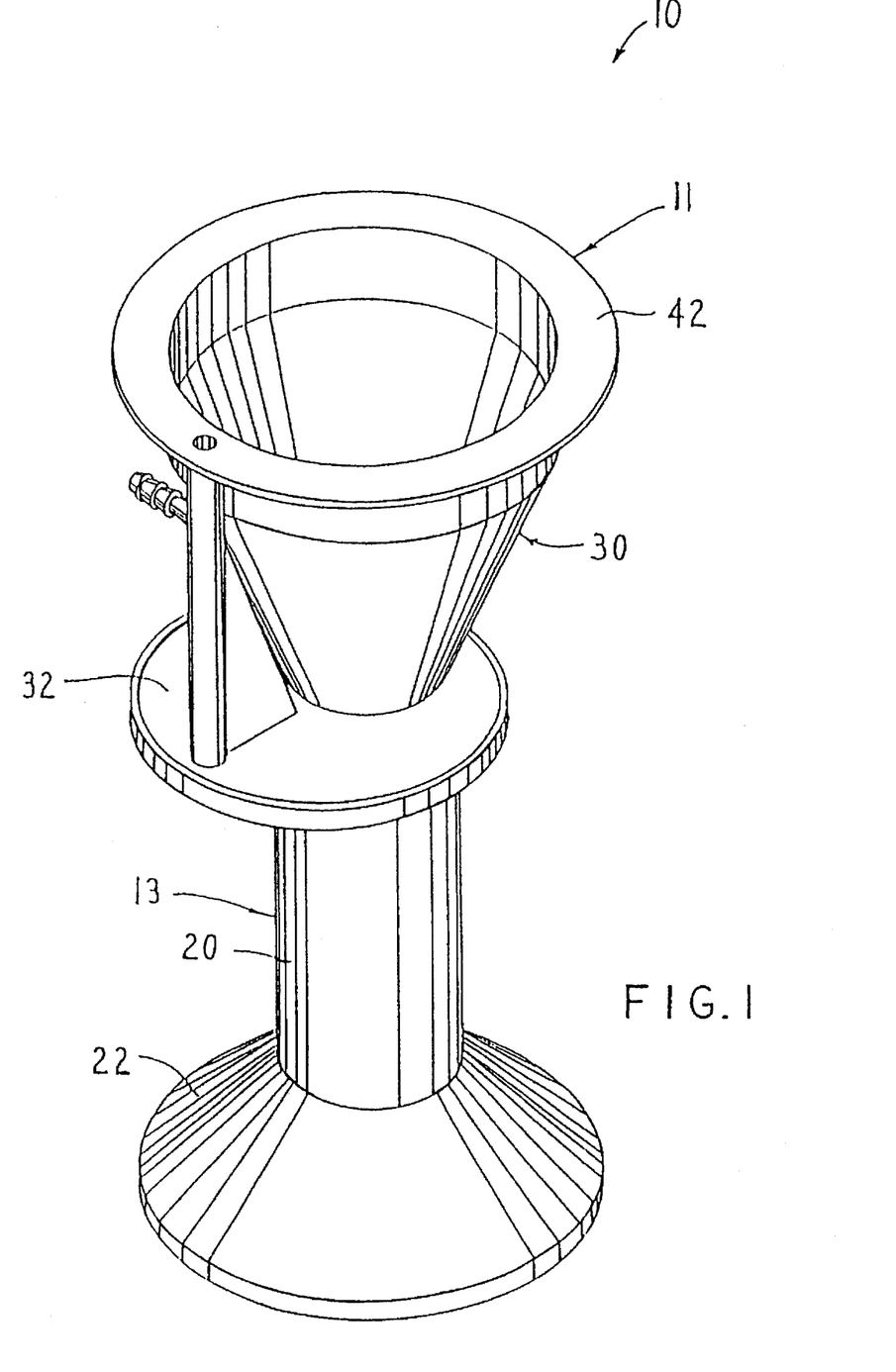
FIG. 1 is a pictorial view of a mixing and loading apparatus of the kind disclosed in aforementioned U.S. application Ser. No. 07/769 004, with the lid assembly removed from atop the mixing chamber, same being shown as an example of apparatus in which the present improvement invention is useable.
Figure 5:
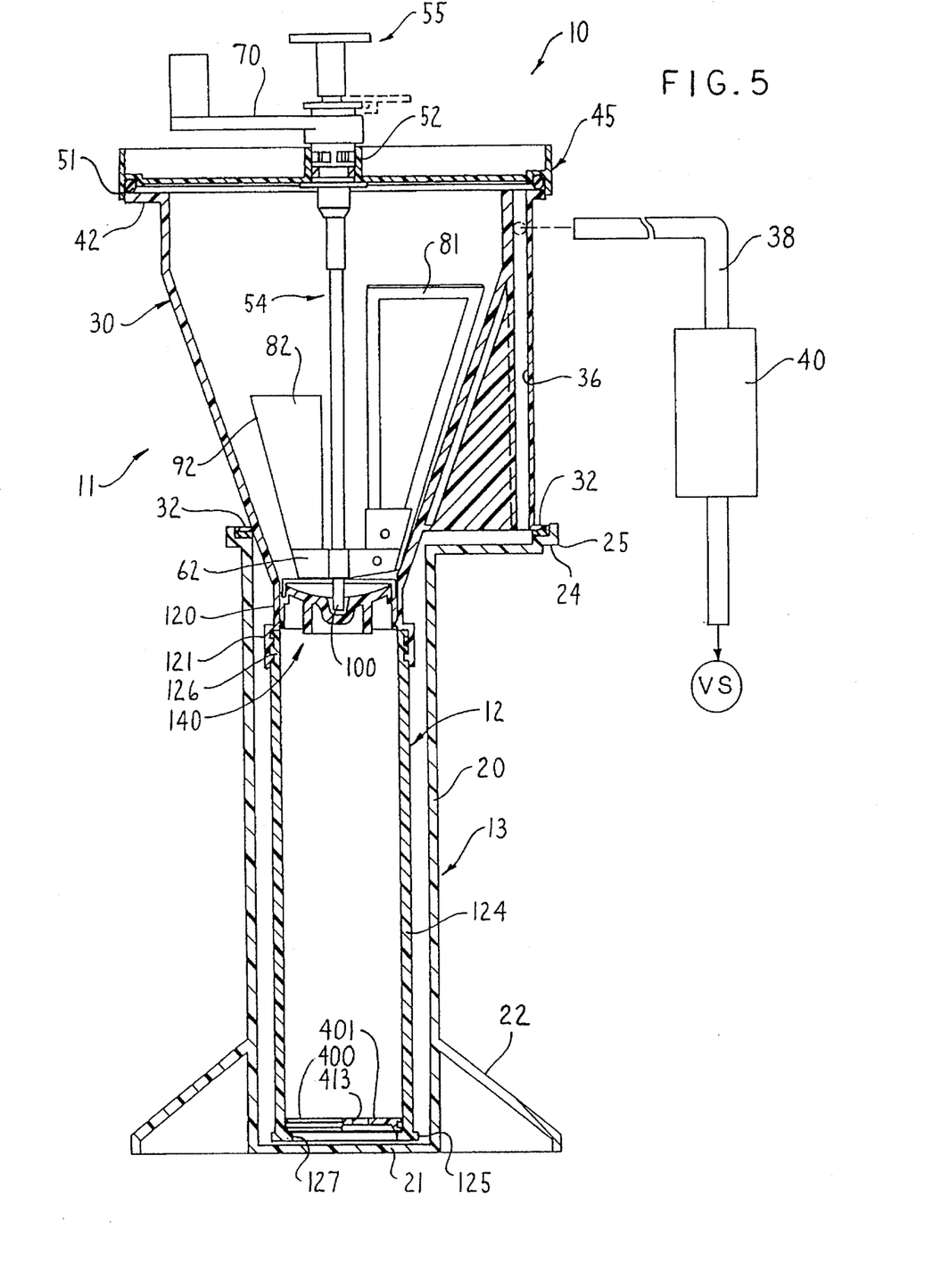
FIG. 5 is an enlarged central cross-sectional view of the FIG. 2 mixing and loading apparatus showing the primary piston and push rod in their upper (preloading) positions and with the secondary piston at the bottom of the cartridge.

The vacuum shroud 13 comprises an upstanding cylindrical casing 20 having a closed bottom 21 and a flared support skirt 22.

The mixing chamber 11 comprises a funnel 30 and a bottom flange 32 which seats on a top flange 24 of the vacuum shroud 13 with an intervening seal ring 25.

A lid assembly 45 seats atop an annular flange 42 at the upper edge of the mixing chamber funnel 30, with an intervening O-ring 51 (FIG. 5). The mixing chamber 11 includes a vacuum passage 36 communicating between the interior of the mixing chamber 30, the interior of the vacuum shroud 13 and a suction tube 38, which through an activated carbon filter 40 connects to a conventional vacuum source VS.

A hub 52 (FIG. 5) on the lid assembly 45 vertically and rotatably supports a hollow shaft assembly 54 pendent coaxially therefrom down into the funnel 30 (when the lid assembly 45 closes the top of the funnel 30 as seen in FIG. 5). The hollow shaft assembly 54 coaxially slideably supports therein a push rod 55. Suitable seals, not shown, are disposed radially between the hub 52, shaft assembly 54 and push rod 55 to prevent air leakage therepast into the funnel 30. A manually rotatable crank handle 70 (FIGS. 2 and 5) is fixed to the top of the shaft assembly 54 and rests atop the lid hub 52 to prevent the shaft assembly 54 from dropping downward with respect to the lid 45. Rotation of the handle 70 positively rotates the shaft assembly 54. The shaft assembly 54 at its bottom includes a rotor 62 fixed for rotation with, and hence by, the handle 70. The rotor 62 comprises a generally upstanding, somewhat tilted out-of-plane, auger 81 and paddle 82. The auger 81 and paddle 82 extend generally upward to the mid-portion of the funnel 30. Rotation of the handle 70 thus rotates the auger 81 and paddle 82 for mixing components of a surgical cement, (e.g. bone cement), the mixed bone cement tending to flow downward to the bottom of the funnel 30 in response to gravity and, in the embodiment shown, assisted by the rotation of the auger 81 and paddle 82.

The push rod 55 extends downward into the hollow shaft assembly 54 so that its lower end 100 protrudes downwardly a short distance beyond the rotative shaft assembly 54. The push rod 55 can be pushed down from its normal beginning position of FIG. 5 to its downwardmost position of FIG. 6 as hereafter described.

The funnel 30 (FIG. 3A) has a cylindrical outlet portion 120 integrally and coaxially dependent from the bottom thereof. An internally threaded connector sleeve 121 integrally and coaxially depends from the cylindrical outlet portion 120 and is internally threaded.

Figure 7:
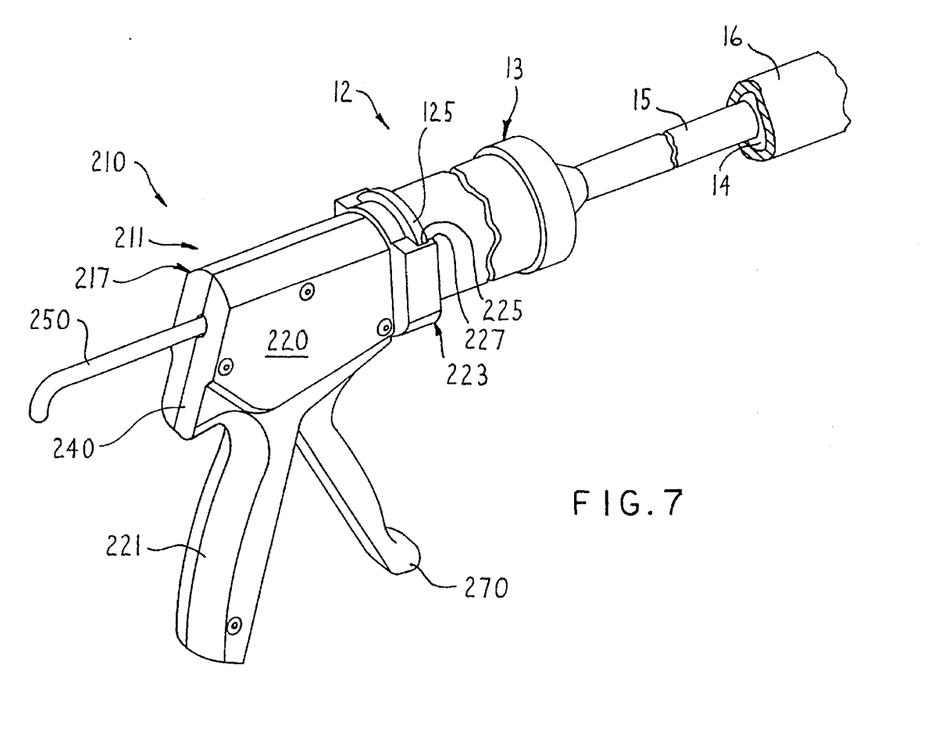
FIG. 7 is a pictorial view of the cartridge of FIGS. 1–6 installed in a gun of the kind disclosed in aforementioned U.S. application Ser. No. 07/769 003 and shown in a position of use for injecting bone cement into the end of a hollow bone, such a femur.
Figure 8:
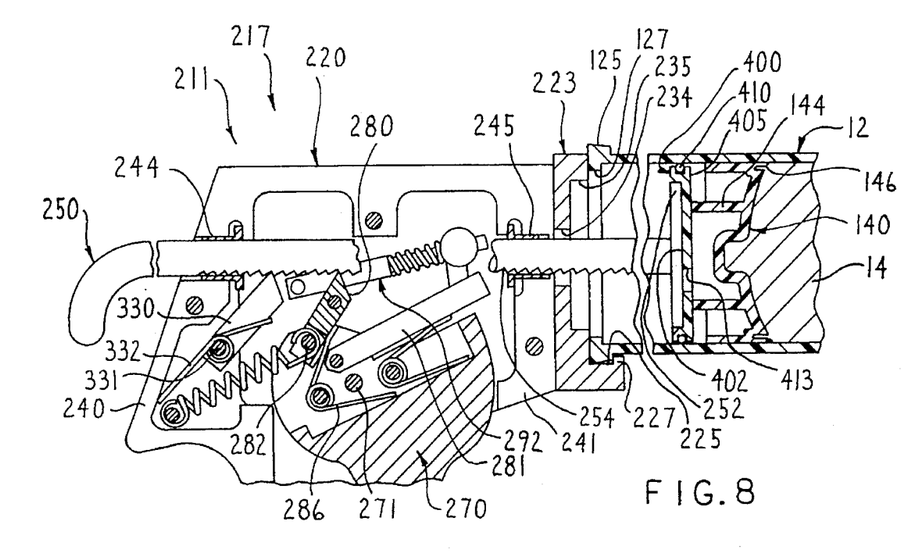
FIG. 8 is an enlarged, partially broken, fragmentary cross-sectional view of the FIG. 7 cartridge and gun.

The cartridge 12 (FIG. 5) comprises a hollow tube 124, open at its upper and lower (front and rear, respectively) ends, and provided at its lower end with a radially outwardly extending flange 125 for removable connection to a cement injection apparatus, as discussed hereafter with respect to FIGS. 7 and 8. The cartridge 12 also has a radially inwardly extending flange 127 at the bottom of the tube 124. The upper end of the cartridge tube 124 is externally threaded at 126. The external threads 126 serve two purposes.

First, during loading of the cartridge 12 with mixed cement, the threaded upper end 126 of the cartridge tube 124 is fixedly but releasably coaxially threaded up into the internal threads 122 of the threaded connector sleeve 121 to fix the cartridge 12 to the bottom of the mixing chamber 11 for filling with cement mixture.

Figure 2:
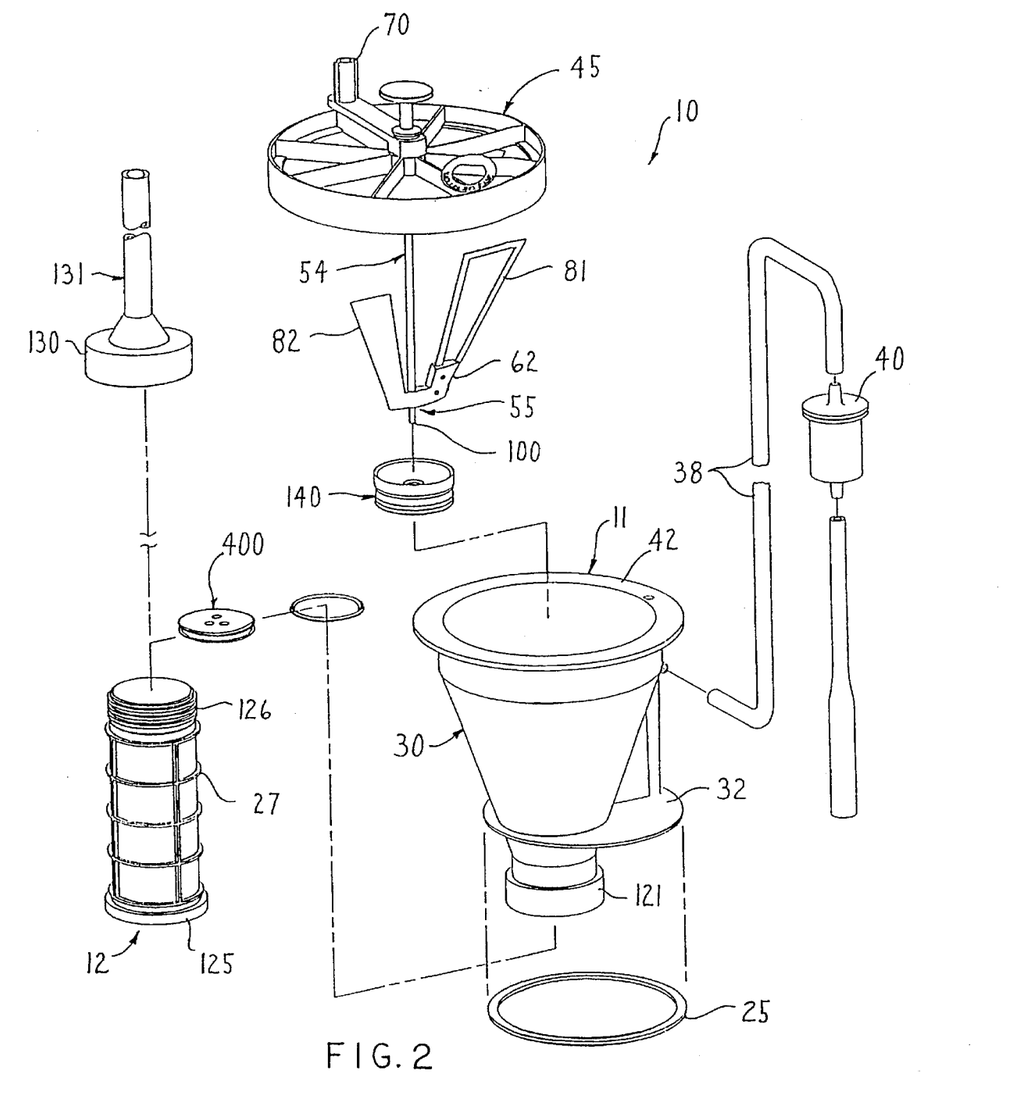
FIG. 2 is an exploded pictorial view of the apparatus of FIG. 1 including the lid assembly and further including a cartridge which embodies the present invention and is to be loaded with bone cement, and further including an outlet nozzle alternatively securable to the cartridge.

Second, the threads 126 on the top of the cartridge 12 threadedly receive, after the cartridge 12 is filled with cement mixture and removed from the mixing apparatus 10, the internally threaded end 130 (FIG. 2) of a cement injection nozzle of any convenient type, e.g. in FIG. 2 at 131. Injector nozzles 131 of different structural configuration can be fitted to the threaded end 126 of the cartridge 12.

The upper portion of the exterior surface of the cartridge 12 may be provided with axially and circumferentially extending reinforcing ribs 27 as seen in FIG. 2, or may be smooth as seen in FIG. 5.

A primary piston 140 (FIG. 3A) has a top 141, a peripheral wall 143 depending from the periphery of the top 141 and an annular cylindrical reinforcing flange 144 depending from the top 141 in radially spaced relation between the peripheral wall 143 and the central axis of the piston. The upper portion (for example the upper one quarter to one third) of the piston peripheral wall 143 is separated, in the central portion of the piston 140, by a narrow upfacing annular groove 145 and thereby forms an upstanding and somewhat radially outwardly biased annular feather seal 146. The annular feather seal radially opposes the surrounding internal cylindrical surface of the lower end portion of the funnel 30 in the upper position of the primary piston shown in FIG. 3A.

Figure 3:
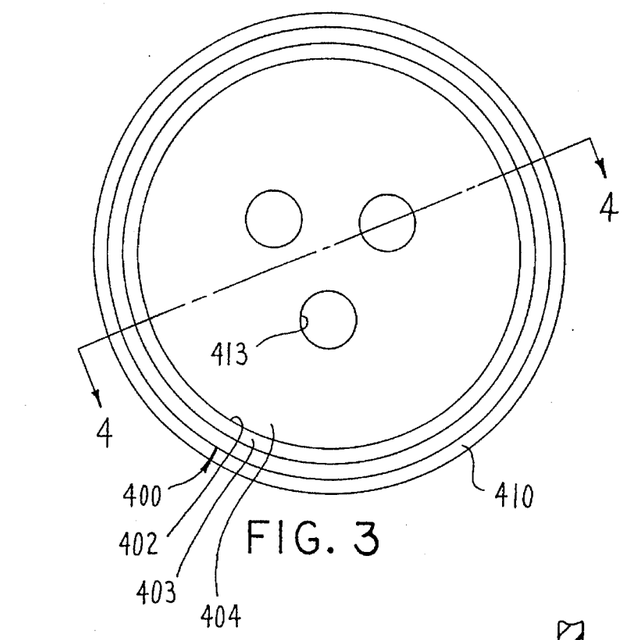
FIG. 3 is an enlarged plan view of the secondary piston of FIG. 2.
Figure 3A:
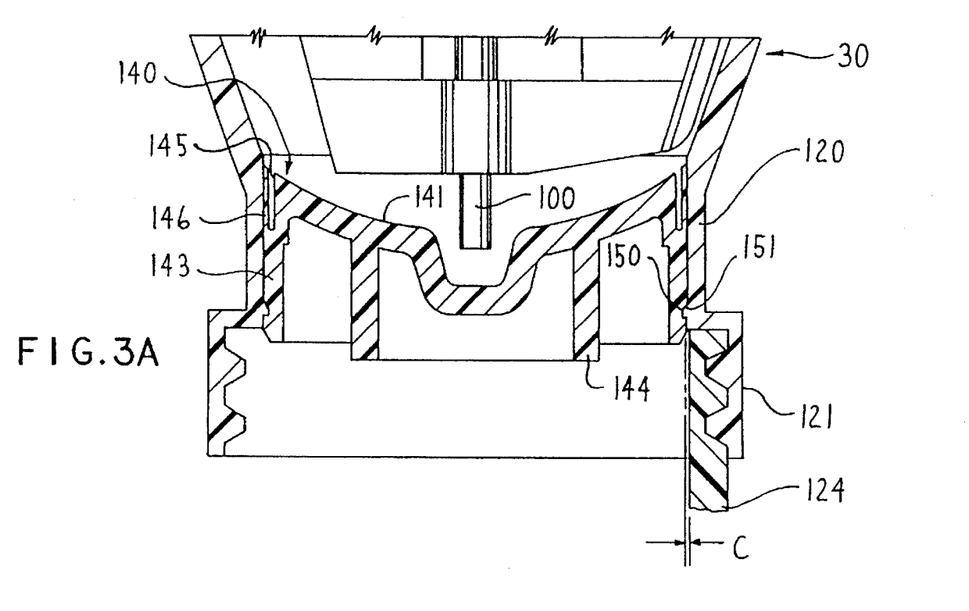
FIG. 3A is an enlarged fragment of FIG. 5 showing the piston at the lower end of the funnel.

The piston 140 is resiliently locked in its upper FIG. 3A position, in the cylindrical outlet of the mixing chamber 11, by a resilient annular detent bead 150 radially inward extending from the interior face of the funnel outlet. The bead 150 snaps into a corresponding outwardly opening annular groove 151 in the bottom half of the peripheral wall 143 of the piston 140. In this position, the piston 140, with its peripheral feather seal 146, plugs the bottom of the mixing chamber 11 prior to and during mixing so that cement components cannot escape from the funnel downwardly into the cartridge 12. After mixing is completed, the user pushes the push rod 55 so its lower end 100 overcomes the resilient detent 150, 151 and displaces the piston 140 downward past the flange 150, out of engagement with the funnel 30 and down into the top of the cartridge tube 124, to its FIG. 6 dotted line position. Rotation of the rotor 62 and the weight of mixed cement are intended to assure movement of the primary piston 140 downward to its FIG. 6 solid line position.

The apparatus 10 is intended to, under a partial vacuum, mix a two-part bone cement and drop the mixed cement into the dispensing cartridge 12 atop the piston 140 therein.

Upon disconnection of the vacuum shroud 13 from the vacuum source VS, the mixing chamber 11, with its depending cartridge 12, can simply be lifted from the vacuum shroud 13 (since a pressure drop from atmospheric to partial vacuum no longer clamps same together). The cartridge 12, filled with cement, can then be unthreaded from the outlet portion 120 of the funnel 30. A nozzle 131 (FIG. 2) is then threaded on the threaded top end 126 of the cartridge 12.

FIGS. 7 and 8 disclose a cement injection apparatus 210 comprising here a generally pistol-shaped device, hereafter conveniently referred to as a gun 211 on which is removably supported the above-described cartridge 12. The cartridge dispensing nozzle 131, or other convenient dispensing nozzle, has its forwardly extending tip 15 shown in FIG. 7 inserted into the surgically opened upper end of a femur 16 of a patient (not shown), for filling the femoral cavity with bone cement 14 preparatory to installation of the stem of an artificial hip replacement prosthesis (not shown) therein.

The gun 211, shown in FIG. 7 by way of example, includes a body 217, which comprises a hollow forward extending receiver 220, from the rear portion of which depends an integral handle 221.

A cartridge support 223 is fixed to the front end (right end in FIGS. 7 and 8) of the receiver 220. The cartridge support 223 has a forward and upward opening recess 225 sized to receive the outer annular flange 125 of the cartridge 12 downwardly slidably therein. A correspondingly oriented, generally U-shaped, radially inward extending flange 227 guards the front end of the recess 225 at the bottom and sides thereof and is open across the top. The flange 227 is sized and shaped to receive downwardly thereinto the sidewall of the cartridge 12 adjacent the outer cartridge flange 125.

To releasably fix the cartridge 12 in forward extending, cantilevered relation on the front end of the gun 211, as shown in FIGS. 7 and 8, the flanged rear end portion of the cartridge is dropped into the cartridge support recess 225 from above. More specifically, the cartridge rear flange 125 is snugly but slideably received down into the cartridge support recess 225 so as to be bounded at its sides and lower portion by the recess perimeter wall. The recess front flange 227 thus positively blocks forward movement of the cartridge with respect to the gun 211 and the cartridge flange 125 is snugly sandwiched axially between the gun recess flange 227 in front thereof and the rearward portion of the body 217. The cartridge 12 is releasably fixed in the cartridge support recess 225 by any convenient means not shown.

A rear opening, central through hole 234 (FIG. 8) extends from the recess 225 rearward through the rear surface of the cartridge support 223. A ram rod 250 extends snugly but slidably forward through bushings 244 and 245 in rear and front walls 240 and 241 of the receiver 220, and then further forward loosely through the central hole 234 of the cartridge support 223. Coaxially fixed to the front end of the rod 250 is a ram disk 252 capable in passing forwardly through the cartridge 12 rear end opening past the interior annular flange 127.

Forward (rightward in FIG. 8) advancement of the ram 250 causes its disk 252 to forwardly advance the primary piston 140 forwardly and thus drive the bone cement 14 forwardly through the tip 15 and into the surgical site, here represented by the end opened femur 16 (FIG. 7).

In the FIG. 8 example, the ram 250 is forwardly advanced by a rack and pawl system. More particularly, a manually actuable trigger 270, disposed in front of the handle 221, is pivoted adjacent its upper end on a transverse pin 271 (FIG. 8) on the receiver 220. A drive pawl 280 has its lower end pivoted by a pivot pin 282 on the trigger 270 at a location spaced above the trigger pivot pin 271. The pawl 280 extends upward and forward from its pivot pin 282, to engage its upper end with rack teeth 254 formed in the underside of the ram 250. A hairpin spring 286 biases the pawl 280 against the rack teeth 254 of the ram 250.

Thus, clockwise pivoting of the trigger 270 (pulling same rearward toward the handle 221) forwards the pawl 280, and hence the ram 250, to forward the primary piston 140, to expel cement 14 through the tip 15 forwardly to the surgical site.

Upon release of the trigger 270, a tension spring 320 (FIG. 8), connected between the receiver 220 and the pin 282 on the trigger 270, pulls the trigger resiliently counterclockwise to its rest position of FIG. 7, dragging the pawl 280 harmlessly rearward, its upper end sliding rearwardly along the tips of the ram teeth 254 to reposition it for a new trigger pull and ram advancement step. The ram 250 cannot move back rearwardly with the rearwardly retracting pawl 280, because a non-return pawl 330 prevents it. More particularly, the non-return pawl 330 has its lower end pivoted on a transverse pin 331 fixed to the receiver 220 and extends forward and upward from pin 331 to engage teeth 254 on the underside of the ram 250, being held against the rack teeth 254 by a further hairpin spring 332.

Aforementioned U.S. application Ser. No. 07/769 003 discloses, in addition, a further drive pawl 281 (FIG. 8) and a switch lever 292 actuable for switching of the ram 250 between the two pawls 280 and 281 to change the forward force on the ram 250, and hence forward pressure to the cement 14, for the same rearward pulling force on the trigger 270. However, the present invention disclosed below is useable without shiftable force changing means and so no further discussion of the further pawl 281 and switch lever 292 is required.

To the extent above described, the apparatus 10 and 210 corresponds respectively to that disclosed in aforementioned U.S. applications Ser. Nos. 07/769 004 and 07/769 003, assigned to the assignee of the present invention. While it is convenient to hereafter disclose the present invention in connection with such apparatus 10 and 210 it will be understood that the present invention is adaptable to use with other mixing/loading and injecting apparatus as well.

Figure 4:
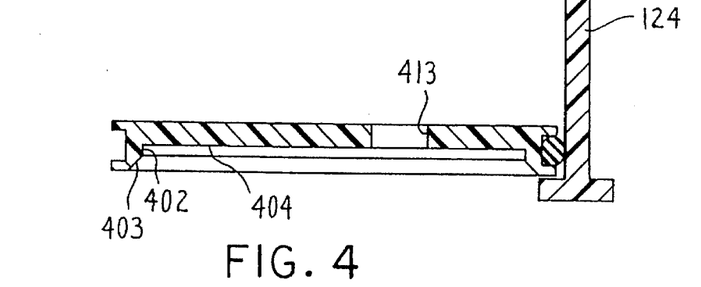
FIG. 4 is a sectional view substantially taken on the line 4—4 of FIG. 3.
Figure 4A:
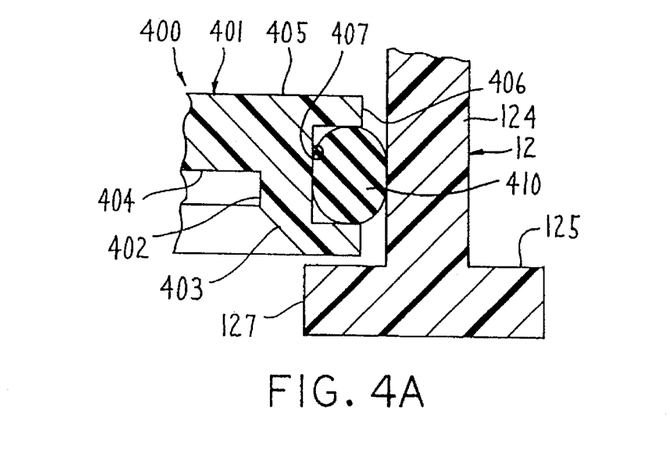
FIG. 4A is an enlarged fragment of FIG. 4.

Turning now to the structure more directly bearing on the present invention, a secondary piston 400 (FIGS. 3, 4 and 4A) comprises a disk 401 preferably flat on one side 405 (the side facing the primary piston 140 in FIG. 5, namely the upper side in FIGS. 4, 4A and 5) and having a central recess 402 in the other side thereof. The edge of the recess 402 is beveled at 403. The recess 402 has a flat bottom 404 parallel to the top surface 405 so that the broad central portion of the disk 401 is of substantially constant cross-sectional thickness.

Holes 413 in the central portion of the secondary piston are evenly circumferentially spaced and located on a constant radius from the central axis of the secondary piston 400 to avoid causing eccentric stresses in the secondary piston 400 during forming and use thereof.

The perimeter 406 (FIG. 4A) of the disk 401 has a substantially rectangular cross-section, annular groove 407. The groove 407 faces radially outward toward the cartridge peripheral wall 24. An elastomeric seal ring 410 occupies the annular groove 407 and bears forcibly and sealingly radially out against the peripheral wall 124 of the cartridge 12. In the preferred embodiment shown, the seal ring 410 is preferably an 0-ring partly radially crushed between the radially opposed surfaces of the cartridge peripheral wall 124 and annular groove 407, to provide a highly effective seal between the secondary piston 400 and the peripheral wall 124 of the cartridge 12, so as to positively preclude bleeding of bone cement 14 rearward past the secondary piston 400 even under the highest expected pressure exertable by the ram disk 252 (FIG. 8) on the cement 14 during all stages of filling of the femur 16 (FIG. 7) with bone cement 14 through the tip 15.

In one unit constructed according to the invention, the O-ring 410 was of 70 durometer silicone rubber having a circular cross-section (when unstressed) partially, radially crushed between the radially opposed surfaces of the groove 407 and cartridge peripheral wall 124. The crush on the O-ring 410 on the secondary piston 400 goes from 0.005" to 0.002" during extrusion of the cement 14 from the cartridge 12.

The secondary piston 400 is of molded rigid plastics material, in the preferred embodiment shown (although a rigid metal secondary piston could be used as well). In one unit constructed according to the invention, the outside diameter of the disk 401 was about 1.495 inch.

OPERATION

The secondary piston 400 is initially located at the bottom (FIG. 5) of the cartridge 12 with the primary piston 140 located at maximum spacing thereabove, prior to insertion of cement components into the mixing chamber 30, as seen in FIG. 5. Following addition of the cement components to the mixing chamber 30, the user places lid assembly 45 atop the mixing chamber 30 to close the top thereof and connects the suction line 38 through filter 42 the vacuum source VS to apply a subatmospheric pressure to the mixing chamber 30 and the interior of the vacuum shroud 13. The holes 413 in the central portion of the disk 401 vent the interior of the cartridge 12 below the primary piston 140 to the vacuum shroud 13 to assure presence of the same subatmospheric pressure above and below the primary piston 140.

Manual rotation of the crank arm 70 causes the paddle 82 and auger 81 to mix the cement components within the mixing chamber 30 and, due to a slight tilting of the auger 81 and paddle 82, helps gravity drive the mixed cement downward toward the primary piston 140. A manual downward push on the push rod 55 releases the primary piston 140 from its detent 150 and slides same downward to its dotted line position shown in FIG. 6, such that the primary piston 140 is now entirely within the upper end portion of the cartridge 12.

Figure 6:
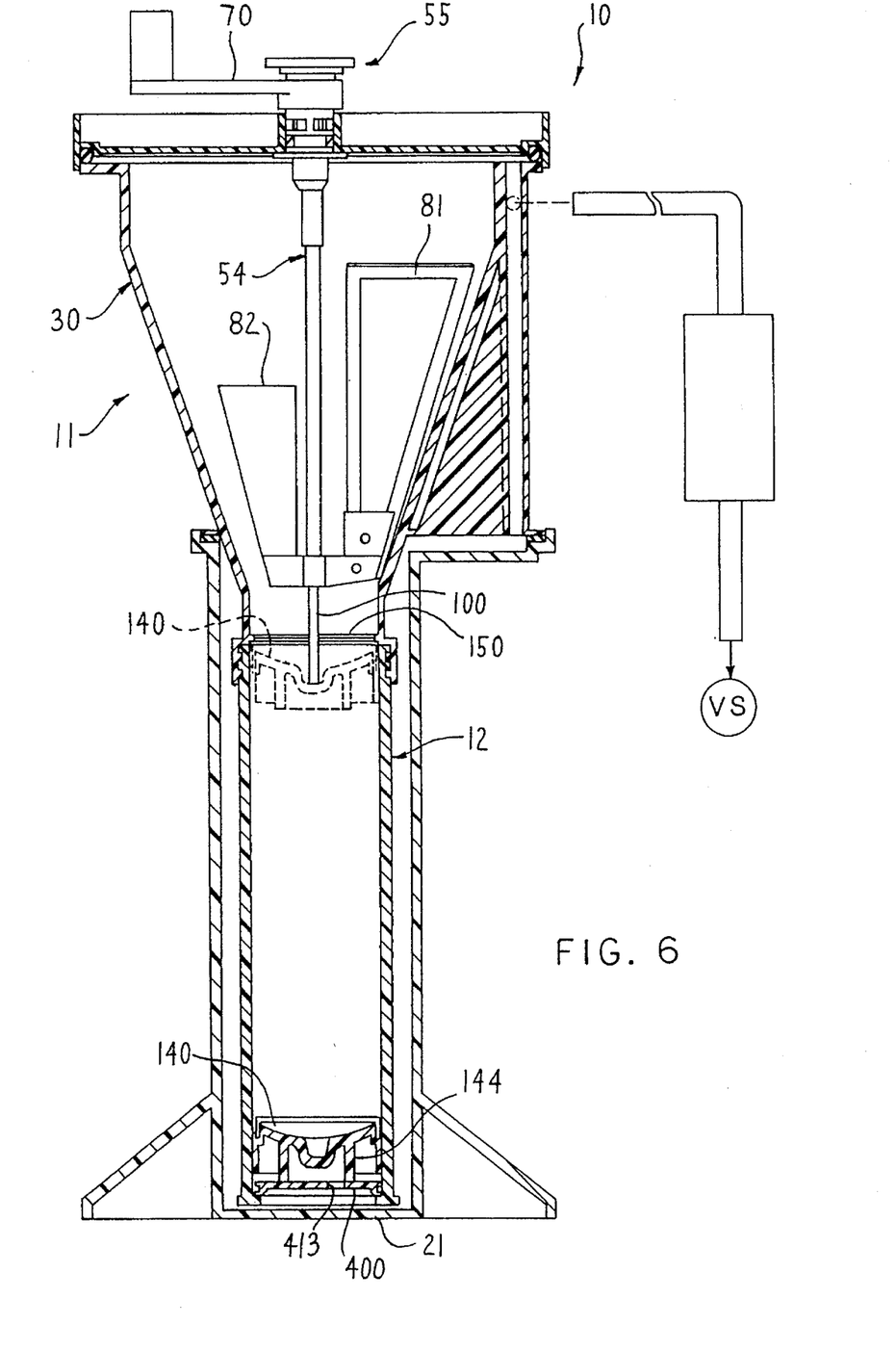
FIG. 6 is a view similar to FIG. 5 but with the push rod in its downward position, with the primary piston shown in dotted line in an intermediate position and in solid line in a downward position adjacent the secondary piston.

Under the present invention, the inside diameter of the cartridge 12 is enlarged to exceed that of the cylindrical out at portion 120 of the funnel 30, in one example by about 0.015 inch. The corresponding difference in radius is shown (exaggeratedly) at C in FIG. 3A. The primary piston 140 can thus be a snug fit in the outlet portion 120 but is now free to slide downward in the cartridge 12 due to its own weight and the weight of cement thereon simply adds to the downward push. Mixed cement from the mixing chamber 30 and the piston 140 thus move by gravity downward from the primary piston dotted line FIG. 6 position toward and eventually into its FIG. 6 solid line bottom position, wherein the primary piston 140 rests atop the secondary piston 400 as shown in FIG. 6. This completes filling of the cartridge 12 with bone cement 14.

Thereafter, the user disconnects the mixing chamber 30 and vacuum shroud 13 from the vacuum source VS, allowing separation of the vacuum shroud 13 from the mixing funnel 30, withdraws the cartridge 12 from the vacuum shroud 13 and unthreads the cartridge 12 from the bottom of the mixing funnel 30. A nozzle 131 is then threaded on the open upper end of the cartridge 12.

Thereafter, the user inserts the bottom end of the cartridge 12 in the cartridge support 223 (FIGS. 7 and 8) of a gun 211, with the ram 250 in its full rearward position wherein the ram disk 252 is recessed (at 235) entirely behind the cartridge 12. The user can then insert the tip 15 into the surgical site, e.g. the open end of a femur 16 as in FIG. 7.

With the ram 250 rotated so that its rack teeth 254 face downward toward the pawls 280 and 330, the user pulls the trigger 270, to clockwise rotate the trigger and cause the drive pawl 280 to advance the ram into the open end (the rear or FIG. 8 leftward end) of the cartridge 12 and bring the ram disk 252 into contact with the secondary piston 400. More particularly, the diameter of the secondary piston recess 402 exceeds the outside diameter of the ram disk 252, so the ram disk 252 seats within the secondary piston recess 402. The flat top (front) surface 405 of the secondary piston 400 bears against the inner annular flange 144 at the bottom of the primary piston 140, such that the forward advancing ram 250 acts through the ram disk 252, the thickness of the central portion of the secondary piston 400 and the primary piston 140 to forcibly drive cement 14 to the forward end of the cartridge 12, through the tip 15 and into the surgical site here exemplified by the open ended femur 16.

It will be noted that the holes 413 in the central portion of the secondary piston 400 are within the radial confines of the inner annular flange 144 of the primary piston 140 and that the ram disk 252 covers such holes 413. Thus, any bone cement 14 that may leak around the exterior of the primary piston, as the ram 250 forces bone cement 14 through the tip 15 into the femur 16, is effectively trapped between the primary piston 140 and secondary piston 400, in the annular space radially outside the inner annular flange 144 of the primary piston. Such leaked bone cement 14 cannot pass radially inward between the inner annular flange 144 of the primary piston and the surface 405 of the secondary piston because of the forcible axial abutment therebetween, as the secondary piston 400 is pressed forward (rightward in FIG. 8) against the inner annular flange 144 of the primary piston 140.

Thus, any leakage of bone cement 14 rearward past the outer periphery of the primary piston 140 would tend to occur during a high pressurization of the bone cement 14 in turn caused by high forward force of the ram 250 on the primary piston 140. However, the same condition maximizes the forward pressure of the secondary piston against the free rear end of the inner annular flange 144 of the primary piston 140 and thereby effectively prevents bone cement 14 leakage radially inward into contact with the central portion of the secondary piston 400.

Indeed, normally the amount of bone cement 14 that may leak rearwardly past the periphery of the primary piston 140 and into contact with the outer portion of the secondary piston 400, radially outboard of the inner annular flange 144 of the primary piston 140, would not come close to filling the annular space radially outboard of the primary piston annular flange 144. Accordingly, that annular space is at substantially atmospheric pressure despite application of much higher pressures to the bone cement 14 by the primary piston 140 as forwardly driven by the advancing ram 250. Accordingly, there is essentially no air pressure drop radially across the annular flange 144, and thus no tendency for bone cement 14 to be pressed radially inward between the primary piston and annular flange 144 and secondary piston 400.

Thus, despite the presence of the vacuum vent holes 413 in the central portion of the secondary piston 400, any bone cement 14 escaping rearwardly past the periphery of the primary piston 140 cannot reach the vacuum holes 413 and hence cannot reach the face of the ram disk 252.

Further, the seal ring 410 surrounding the secondary piston 400 positively prevents the escape bone cement 14 from passing rearwardly beyond the periphery of the secondary piston 400. The secondary piston 400 is diametrally sized such that its seal ring 410 maintains an effective seal against the interior of the peripheral wall of the cartridge 12 along the entire length of the cartridge 12, despite abnormal variations in interior cartridge diameter (due for example to normal manufacturing tolerances in molding of the peripheral wall of the cartridge 12 and possible small internal taper of the cartridge peripheral wall for mold release purposes). Thus, the secondary piston 400 and its annular seal ring 410 are sized to maintain sealing contact, with at least some radial crush of the resilient seal ring 410, throughout the length of movement of the secondary piston 400 along the length of the cartridge 12, during forcible unloading of bone cement 14 from the cartridge 12 to the surgical site 16.

The ability of the secondary piston to isolate leaked bone cement 14 from the ram disk 252, ram 250, and remainder of the gun 211 eliminates any possibility of cement contamination of the gun 211 and need to clean the gun after use with a given cement cartridge, even if the primary piston 140 thereof suffers rearward leakage of bone cement 14 past the periphery thereof.

The contact of the seal ring 410 with the interior surface of the cartridge peripheral wall provides some frictional resistance to forward movement of the secondary piston 400 along the length of cartridge 12. However, that axial frictional resistance force is negligible compared to the forward force applied by the ram 250 to the secondary piston 400 and primary piston 140 to force bone cement 14 from the cartridge 12 through the tip 15 and into the cavity of the femur 16.

In view of the capability of the secondary piston 400 to prevent contamination of the gun 211 (including the ram 250 and ram disk 252) by any bone cement 14 that may escape rearwardly past the perimeter of the primary piston 140, during high pressure cement injection to a surgical site 16 (FIG. 7), the annular feather seal 146 of the primary piston 140, during filling (FIGS. 5 and 6) of the cartridge 12, need not push radially outwardly heavily against the cartridge peripheral wall. More particularly, the annular feather seal 146 here slightly radially clears or brushes only lightly against the cylindrical peripheral wall 124 of the cartridge 12 so as easily drift downwardly therealong merely under its own weight, and certainly under the weight of the bone cement in the chamber 30. Thus, the primary piston 140 can be diametrally sized to reliably drift downward along the height of the cartridge 12 during loading of the cartridge with bone cement without any danger of hanging up partway downward and despite normal irregularities or mold draft taper in the interior surface of the peripheral wall 124 of the cartridge. Despite the resulting elimination of friction between the primary piston 140 and the surrounding peripheral wall 124 of the mixing chamber outlet 120 and cartridge 12 during loading (FIGS. 5 and 6), there is no significant tendency of bone cement leak downward past the periphery of the primary piston 140 because (1) air pressure above and below the primary piston 140 is equalized (the same subatmospheric pressure being applied to both top and bottom of the primary piston 140), (2) the sole downward force of bone cement on piston being gravitational and hence relatively light, and (3) the primary piston 140 is free to drift downwardly within the cartridge 12.

Thus, the flexible annular feather seal 146, lever-like in cross-section as seen in FIG. 3A, here bears only very lightly, at most, against the interior wall of the casing during gravitational loading of the casing with bone cement atop the primary piston. However, despite this, during unloading of bone cement under pressure of the ram 250, as discussed with respect to FIGS. 7 and 8, the highly pressurized cement 14 tends to fill and radially widen the scoop-like, forward opening, annular groove 145 and thus bend the feather seal 146 radially out toward the interior wall of the casing, to enhance sealing and limit cement leakage rearward past the primary piston 140 toward the secondary piston 400.

Thus, the presence of the secondary piston 400 allows easy and reliable loading of the cartridge 12 with bone cement merely under the weight of the bone cement and yet positively precludes bone cement contamination of the interior of the gun 211 (including the ram disk 252 and ram 250) during ejection of bone cement, even under very high pressure, through the tip 15 into the surgical site 16. The lack of contamination of the gun 211 by bone cement is particularly valuable because it would be time consuming and difficult to move hardened bone cement from interior surfaces of the gun 211. Whereas the cartridge 12 is disposable after a single use, it is desirable to be able to reuse the gun 211 a number of times. Such reuse would be hampered by the need to clean bone cement from the gun 211 after a given use.

The recessing of one side of the secondary piston 400 minimizes the axial space the secondary piston takes within the cartridge 12, so as to (1) not significantly reduce the amount of bone cement receivable within the cartridge 12, (2) minimize the amount of material required to mold the secondary piston, and (3) allow the cartridge 12 equipped with such a secondary piston 400 to be used with a gun 211 designed for use without a secondary piston in the cartridge 12 without risking jamming of the pistons 140 and 400 hard against the nozzle 131 with the non-return pawl 330 locked hard against a tooth 254 of the ram 250.

By allowing the ram disk 252 to enter the recess 402 of the secondary piston 400, and indeed providing the bevel 403 to help guide such entry, the secondary piston assists in maintaining the cantilevered forward end of the ram 250 coaxial with the cartridge 12 during advancement of the ram 250 toward the distant forward end of the cartridge 12, as the last of the bone cement 14 is unloaded from the cartridge into the tip 15 on the way to the surgical site 16.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. A surgical cement cartridge for loading with surgical cement and for ejecting surgical cement at a surgical site, the cartridge comprising:

a substantially tubular casing comprising a peripheral wall surrounding a longitudinal passage, the passage having an open front end and a remote rear end;

a first piston means located in said passage for free sliding movement from said front end towards said rear end in response to input of surgical cement into said front end of said casing;

a second piston means located in said passage adjacent said rear end for forcible driving forward along said passage to cause said first piston means to eject cement from said open front end of said casing toward a surgical site, said second piston means having seal means for positively blocking flow of surgical cement axially therepast, said seal means comprising an elastomeric annular seal which bears forcibly and sealingly and slidingly against said casing peripheral wall.

2. The apparatus of claim 1 in which said first piston means comprises a primary piston having a starting position adjacent the front end of the casing and arranged for movement longitudinally of said casing toward a rear end of said casing and having a cement-loaded position adjacent the rear end of said casing, said primary piston having a front face engageable by surgical cement loaded into the front end of the casing, said primary piston having a annular peripheral means closely radially opposing an interior wall of said casing for allowing said primary piston to move from its front position to its rear position freely in response to the weight of surgical cement loaded in the front end of said cartridge against the front face of said primary piston, said second piston means comprising a secondary piston having a starting position between the rear position of said primary piston and the rear end of said casing, said seal means comprising an annular seal radially interposed between the periphery of said secondary piston and the interior wall of said casing, such that said secondary piston differs from said primary piston in having (1) a radially tighter fit within the casing, (2) greater frictional resistance to axial movement along said casing, and (3) a more positive seal against migration of surgical cement axially therepast toward the rear end of said casing, said secondary piston having rear end means engageable by a forward moving ram of a cement injection device for causing said secondary piston to (1) move forwardly along said casing, (2) push said primary piston from its rearward position forwardly along said casing toward its front position, and (3) push surgical cement ahead of said primary piston forward out of said casing toward a surgical site.

3. The apparatus of claim 1 including means at said front end of said casing for connection beneath a gravity flow outlet of a surgical cement mixer unit, said first piston means having seal means engaging the interior face of the casing peripheral wall lightly for gravitational driving down of said first piston means substantially in response to the weight of surgical cement loaded in the front end of said cartridge atop a front face of said first piston means, said second piston seal means differing from said first piston seal means in having (1) a radially tighter fit within the casing, (2) greater frictional resistance to axial movement along said casing, and (3) a more positive seal against migration of surgical cement axially therepast toward the rear end of said casing.

4. The apparatus of claim 3 in which said second piston is axially thin and wafer-like compared to said first piston, said casing rear end including port means for receiving axially forwardly therethrough a ram of a cement injection apparatus, said second piston having rear face means for receiving axially forwardly thereagainst the same ram, said casing rear end having radially inward flange means engaging and positively locating said second piston at the bottom of said casing during loading of the casing with surgical cement, the relative thinness of said second piston allowing dropping of said first piston substantially to the bottom of said casing, the axial space occupied at the bottom of the casing by said second piston being a small fraction of the axial space occupied by said first piston and permitting maximizing of the volume of cement loaded into said casing.

5. The apparatus of claim 1 in which said first and second piston means comprises first and second pistons respectively, said first piston having seal means only relatively lightly engaging said casing and movable freely downward in said casing in response to the weight of surgical cement atop said first piston with said casing open front end up and rear end down, said first piston seal means tending to impede cement leakage downward therepast under the force of gravity, said second piston seal means more tightly engaging said casing to prevent leakage rearward therepast into a reusable ram forwarding gun of any cement that may have leaked past said first piston into the portion of said casing between said pistons, even with said second piston and thereby said first piston rammed forward with a force substantially greater than that of gravity.

6. The apparatus of claim 5 in which said first piston seal means comprises an upstanding integral feather seal spaced radially outward from the remainder of said first piston by a forward opening groove and said second piston seal means comprising an O-ring-type seal protruding radially outward from a radially outward opening groove in the rim of said second piston.

7. The apparatus of claim 1 in which said first piston means has seal means for impeding flow of surgical cement rearwardly therepast, such that both said piston means have respective seal means.

8. A surgical cement cartridge for loading with surgical cement and for ejecting surgical cement at a surgical site, the cartridge comprising:

a substantially tubular casing comprising a peripheral wall surrounding a longitudinal passage, the passage having a front inlet/outlet end and a remote rear end;

a first piston means located in said passage for free sliding movement from said front end towards said rear end in response to input of surgical cement into said front end of said casing, said first piston means having perimeter means radially opposing the interior surface of said casing for allowing free longitudinal movement of said piston in said passage but limiting leakage of cement sealingly therepast toward rear end;

a second piston means located in said passage adjacent said rear end, said second piston means having annular seal means at its perimeter and pressing radially outward against the peripheral wall of said casing for positively blocking flow of surgical cement axially therepast toward said rear casing end but for forcible driving axially along said passage towards said first end of said casing by a cement injection means to cause said first piston means to eject cement toward a surgical site, said seal means comprising an elastomeric annular seal which bears forcibly and sealingly an slidingly against said casing peripheral wall, and in which the force required to move said second piston means in said cartridge exceeds the force required to axially move said first piston means towards said casing rear end.

9. The apparatus of claim 8 in which said first piston means is a clearance fit and said second piston means is an interference fit in said casing.

10. The apparatus of claim 8 in which the axial force required to move said first piston means toward said rear casing end corresponds to the weight of cement to substantially fill said cartridge and the force required to move second piston means in said cartridge substantially exceeds the force required to axially move said first piston means towards said casing rear end.

11. The apparatus of claim 8 in which said casing has a radially inward extending annular flange adjacent the rear end thereof and defining a forward facing step for blocking rearward displacement of said second piston means out of said casing.

12. A surgical cement cartridge for loading with surgical cement and for ejecting surgical cement at a surgical site, the cartridge comprising:

a substantially tubular casing comprising a peripheral wall surrounding a longitudinal passage, the passage having a front inlet/outlet end and remote rear end:

a first piston means located in said passage for free sliding movement from said front end towards said rear end in response to input of surgical cement into said front end of said casing, said first piston means having perimeter means radially opposing the interior surface of said casing for allowing free longitudinal movement of said piston in said passage but limiting leakage of cement sealingly therepast toward rear end;

a second piston means located in said passage adjacent said rear end, said second piston means having annular seal means at its perimeter and pressing radially outward against the peripheral wall of said casing for positively blocking flow of surgical cement axially therepast toward said rear casing end but for forcible driving axially along said passage towards said first end of said casing by a cement injection means to cause said first piston means to eject cement toward a surgical site; and means for applying suction to both ends of said cartridge during filling with cement for minimizing gas bubbles in surgical cement in said cartridge, said second piston means including an axial through hole radially inboard of said annular seal means for application of suction to both ends of said first piston means.

13. The apparatus of claim 12 in which said axial through hole is in the central portion of said second piston means, said first and second piston means having mutual abutting contact surface means surrounding said axial through hole in said second piston means for preventing escape of surgical cement trapped between said first and second piston means through said axial through hole in said second piston means out through said rear casing end and away from a surgical site.

14. A surgical cement cartridge for loading with surgical cement and for ejecting surgical cement at a surgical site, the cartridge comprising:

a substantially tubular casing comprising a peripheral wall surrounding a longitudinal passage, the passage having a front inlet/outlet end and a remote rear end;

a first piston means located in said passage for free sliding movement from sad front end towards said rear end in response to input of surgical cement into said front end of said casing, said first piston means having perimeter means radially opposing the interior surface of said casing for allowing free longitudinal movement of said piston in said passage but limiting leakage of cement sealingly therepast toward rear end;

a second piston means located in said passage adjacent said rear end, said second piston man having annular seal means at its perimeter an pressing radially outward against the peripheral wall of said casing for positively blocking flow of surgical cement axially herepast toward said rear casing end but for forcible during axially long said passage towards said first end of said casing by a cement injection means to cause said first piston means to eject cement toward a surgical site, said second piston means having a rear facing recess for receiving a cement injection means ram advanceable through an opening in said rear end of said casing into nested relation in said second piston means recess for (1) forwarding said second piston means to inject cement from said cartridge toward a surgical site, (2) minimizing the thickness of said second piston means between a ram and said first piston means, (3) limiting radial displacement of a ram with respect to said casing as such a ram travels along said casing toward the front end thereof, (4) permitting axial elongation of the perimeter of said second piston means beyond the axial thickness of the central portion of said second piston means to support said annular seal means on the perimeter of said second piston means adequate for positively blocking leakage of surgical cement rearwardly along said casing therepast, and (5) helping prevent locking of a ram in a forwardmost position in said cartridge.

15. A surgical cement cartridge for loading with surgical cement and for ejecting surgical cement at a surgical site, the cartridge comprising:

a substantially tubular casing comprising a peripheral wall surrounding a longitudinal passage, the passage having a front inlet/outlet end and a remote rear end;

a first piston means located in said passage for free sliding movement from said front end towards said rear end in response to input of surgical cement into said front end of said casing, said first piston means having perimeter means radially opposing the interior surface said casing for allowing free longitudinal movement of said piston in said passage but limiting leakage of cement sealingly therepast toward rear end;

a second piston means located in said passage adjacent said rear end, said second piston means having annular seal means at its perimeter and pressing radially outward against the peripheral wall of said casing for positively blocking flow of surgical cement axially therepast toward said rear casing end but for forcible driving axially along said passage towards said first end of said casing by a cement injection means to cause said first piston means to eject cement toward a surgical site, said first piston means having a rearward extending generally tubular portion spaced radially inboard from the casing peripheral wall, said second piston means having an air venting axial through hole surrounded by a forward facing annular surface portion in turn abutted by an annular rear edge of said tubular portion, with said first piston means backed against said second piston means.

16. A surgical cement cartridge for loading with surgical cement and for ejecting surgical cement at a surgical site, the cartridge comprising:

a substantially tubular casing comprising a peripheral wall surrounding longitudinal passage, the passage having an open front inlet/outlet end and a remote rear end;

a first piston means located in said passage for free sliding movement from said front end towards said rear end in response to input of surgical cement into said front end of said casing, said first piston means having perimeter means radially opposing the interior surface of said casing for allowing free longitudinal movement of said piston in said passage but limiting leakage of cement sealingly therepast toward rear end;

a second piston means located in said passage adjacent said rear end, said second piston means having annular seal means at its perimeter and pressing radially outward against the peripheral wall of aid casing for positively blocking flow of surgical cement axially therepast toward said rear casing end but for forcible driving axially along said passage towards said first end of said casing by a cement injection means to cause said first piston means to eject cement toward a surgical site; and cement loading means comprising a generally cylindrical outlet for snugly receiving said first piston means and detent means for initially holding said first piston means to close the bottom of said cement loading means, means for releasibly connecting the open front end of said casing to said cement loading means cylindrical outlet below said initial position of said first piston means, means for driving said first piston means out of said cement loading means outlet and into the open front end of said cartridge to open the cement loading means outlet to said cartridge and to permit surgical cement in said cement loading means to flow through said outlet into said cartridge atop said first piston means, the first piston means being a snug radial fit in said cement loading means outlet to resist leakage of cement downwardly through said cement loading means outlet past said first piston means, the inside diameter of said cartridge exceeding the inside diameter of said cement loading means outlet to-provide a clearance radially between said first piston means and the interior surface of said casing sufficient to allow said first piston means to move downward by gravity in said cartridge casing from said front end thereof towards said rear end thereof.

* * * * *

UNITED STATES PATENT AND TRADEMARK OFFICE
CERTIFICATE OF CORRECTION

PATENT NO. : 5 558 136
DATED : September 24, 1996
INVENTOR(S) : Michael R. ORRICO It is certified that error appears in the above-indentified patent and that said Letters Patent is hereby corrected as shown below:

```
Column 12, line 11; change "an" to ---and---.
Column 13, line 18; change "man" to ---means---;
        line 22; change "herepast" to ---therepast---;
        line 23; change "during" to ---driving---;
        line 24; change "long" to ---along---; and
        line 56; change "surface said" to ---surface of
            said---.
Column 14, line 17; change "surrounding longitudinal"
            to ---surrounding a longitudinal---;
        line 31; change "aid" to ---said---; and
        line 56; change "to-provide" to ---to provide---.
```

Signed and Sealed this

Eighteenth Day of November 1997

*Attest:*

BRUCE LEHMAN

*Attesting Officer*  *Commissioner of Patents and Trademarks*